United States Patent [19]

Hamilton-Miller

[11] Patent Number: 5,879,683
[45] Date of Patent: Mar. 9, 1999

[54] ANTIBACTERIAL AGENT CONTAINING TEA EXTRACT OR ACTIVE FRACTION THEREOF AND β-LACTAM ANTIBIOTIC

[75] Inventor: Jeremy Marcis Tom Hamilton-Miller, London, United Kingdom

[73] Assignee: Royal Free Hospital School of Medicine, United Kingdom

[21] Appl. No.: 704,629

[22] PCT Filed: Mar. 3, 1995

[86] PCT No.: PCT/GB95/00461

§ 371 Date: Sep. 25, 1996

§ 102(e) Date: Sep. 25, 1996

[87] PCT Pub. No.: WO95/23607

PCT Pub. Date: Sep. 8, 1995

[30] Foreign Application Priority Data

Mar. 4, 1994 [GB] United Kingdom .................... 9404303

[51] Int. Cl.⁶ .................... A61K 39/385; A61K 39/38; A61K 39/02; A61K 39/09
[52] U.S. Cl. .................... 424/195.11; 424/184.1; 424/234.1; 424/237.1; 514/1; 514/2
[58] Field of Search .................... 424/195.11, 184.1, 424/234.1, 237.1; 514/1, 2

[56] References Cited

U.S. PATENT DOCUMENTS 5,610,139  3/1997  Ohta et al. .................... 514/13

FOREIGN PATENT DOCUMENTS

A 0443090  8/1991  European Pat. Off. .

OTHER PUBLICATIONS

Robertson, et al.: Production and HPLC analysis of Black tea theaflavins . . . : Phytochemistry: vol. 22, No. 4: pp. 883–887, 1983.

Database WPI, Section Ch, Week 9107 Derwent Publications Ltd., London, GB; Class A96, AN91–047285 & JP–A–02 311 474 (Ito En KK), 27 Dec. 1990.

Database WPI, Section Ch, Week 9008 Derwent Publications Ltd., London, GB; Class B04, AN 90–054131 & JP–A–02 006 499 (Taiyo Kagaku KK), 10 Jan. 1990.

*Primary Examiner*—Lynette F. Smith
*Assistant Examiner*—Brem Nelson
*Attorney, Agent, or Firm*—Nixon & Vanderhye

[57] ABSTRACT

The invention provides a method of inhibiting production of bacteria which constitutively express PBP2' or bacteria which inducibly express PBP2' in the presence of a β-lactam antibiotic, by administering an effective amount of an extract of tea to the bacteria. The tea extract contains at least one active principle of dried tea and being extractable from processed dried tea with hot water and this active principle is capable, on administration, of restoring the activity against methicillin-resistant *Staphylococcus aureus* (MRSA) of a β-lactam antibiotic. Preferably, the extract of tea can be administered to a human or animal subject together with a β-lactam antibiotic.

12 Claims, 1 Drawing Sheet

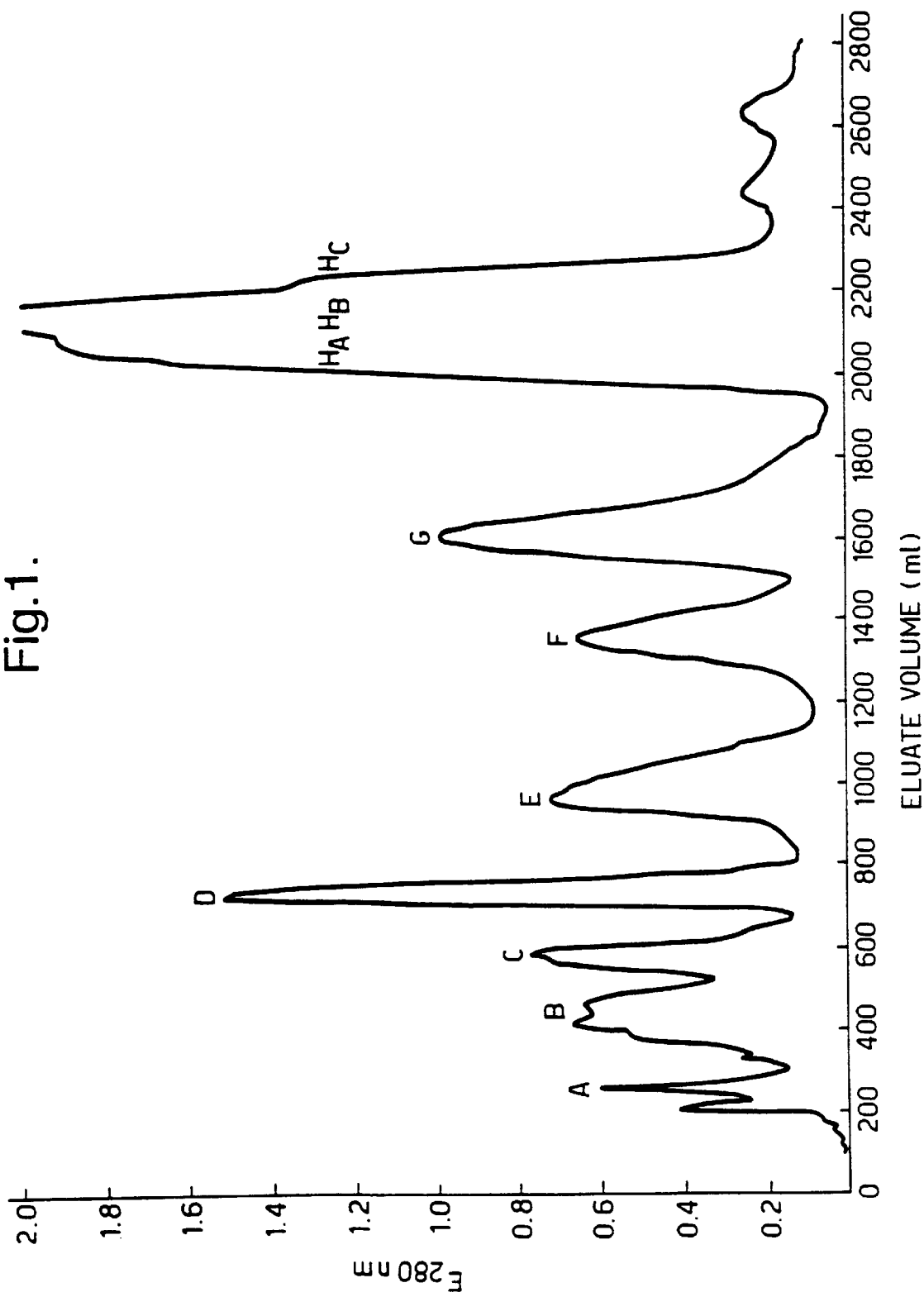

ANTIBACTERIAL AGENT CONTAINING TEA EXTRACT OR ACTIVE FRACTION THEREOF AND β-LACTAM ANTIBIOTIC

The present invention relates to a novel composition with antibacterial activity and its use. In particular, the composition has activity against methicillin-resistant *Staphylococcus aureus* (MRSA).

*Staphylococcus aureus* is a gram-positive bacteria which is recognised in the clinical microbiology laboratory by its ability to make coagulase. *S. aureus* is often carried by humans. Reference may be made to Bergey's manual of Determinative Bacteriology (9th edition, 1993) for details of further classification of *S. aureus*. *S. aureus* may acquire resistance to antibiotics. Patients in hospitals can become infected with MRSA which can lead to serious illness or even death. Strains of *S. aureus* which can be considered resistant to methicillin are those strains in which growth occurs in the presence of 8 μg/ml methicillin (National Committee for Clinical Laboratory Standards, 1990—Methods for dilution antimicrobial susceptibility tests for bacteria that grow aerobically (second edition). Document M7-A2. NCCLS, Villanova, Pa., U.S.A.).

MRSA are pathogens of major and growing importance. They are set apart from other *Staph. aureus* by their resistance to all antibiotics of β-lactam group—e.g. penicillins and cephalosporins. These compounds act on sensitive strains by binding to bacterial proteins called "Penicillin Binding Proteins" (PBPs). In MRSA, one particular PBP, namely PBP2', has altered to such an extent that β-lactam antibiotics bind poorly to it. PBP2' is thus the key to resistance in MRSA. In addition, *Staph. aureus* has the ability to produce the enzyme β-lactamase. This ability is present in both MRSA and non-methicillin-resistant *Staph. aureus*. This enzyme destroys benzylpenicillin and ampicillin. Other β-lactam antibiotics such as methicillin or cephalothin are resistant to β-lactamase.

Infections with MRSA can be treated with a group of antibiotics called the glycopeptides; these are expensive and potentially toxic. What is most worrying is that this is the only widely available treatment; resistance to the glycopeptides has emerged in closely related bacteria, and could easily emerge too in MRSA.

From a clinical point of view, glycopeptides such as vancomycin have to be used to treat MRSA; however, the more they are used, the more likely is glycopeptide resistance to emerge. This would leave a lack of any reliable treatment for MRSA infections.

Other types of staphylococcus have methicillin-resistant strains, some of which are resistant due to the presence of PBP2'. Examples are *Staph. epidermidis* and *Staph. haemolyticus*, both of which are coagulase negative species.

It has been found that an extract of tea has antibacterial properties. For example, EP-A443,090 shows that an extract of tea at a concentration of about 0.2–2.0 g/100 ml is capable of preventing the growth of a number of types of bacteria, including some strains of MRSA.

In this context, tea refers to the dried, processed leaves of the plant *Camellia sinensis*. This plant is regarded as a single species, although botanical variants occur and two varieties are recognised: *assamica*, a large-leaved (15–20 cm) plant and *sinensis*, a smaller-leaved (5–12 cm) variety. The growing point of the plant, consisting of terminal buds and immature leaves (known technically as "flush"), is picked. Green tea (such as "Sencha" tea) is made from flush by heating, macerating and drying in hot air until the moisture content is reduced to 34%. Black tea is made by allowing flush to wither until the moisture content falls to 50–60% after which it is macerated and then "fermented". This occurs by spreading tea thinly and allowing it to stand at room temperature for 1–3 hours. During this time it turns black due to the action of catechol oxidase on the polyphenols. It is then dried in hot air until the moisture content reaches 3%. A further type of tea, oolong tea, is prepared using a partial fermentation. The processing of tea is described in further detail in the Kirk-Othmer Encyclopedia of Chemical Technology (third edition, 1983), pub. John Wiley & Sons.

It has now been found that an extract of tea is not only capable of inhibiting MRSA but also restoring the activity of methicillin against MRSA. Thus, it has been found that an extract of tea acts synergistically with methicillin against MRSA. This synergistic activity of tea extract against MRSA is believed to be a combination of three component activities.

Firstly (activity I), an extract of tea inhibits or kills MRSA.

Secondly (activity II), an extract of tea has an activity against PBP2': While not wishing to be bound by any one particular theory it is believed that the tea extract inhibits PBP2' formation in MRSA, allowing methicillin (and other β-lactam antibiotics) to act against these pathogens. This mode of action means that other methicillin-resistant bacteria (particularly other staphylococci) which are resistant due to the presence of PBP2' will also be susceptible to the synergistic action of tea and methicillin.

Thirdly (activity III), it has also been found that an extract of tea is capable of inhibiting the β-lactamase activity of *Staph. aureus*, including MRSA. Thus an extract of tea acts synergistically with a β-lactam antibiotic, including benzylpenicillin or ampicillin.

The present invention therefore provides a product comprising a synergistic combination of an extract of tea or active fraction thereof and a β-lactam antibiotic as a combined preparation for simultaneous, separate or sequential use in the treatment of MRSA infections in animals including man.

More specifically, the invention provides a product as defined above, wherein the extract of tea is obtainable by (a) extracting tea into an aqueous medium;

(b) removing solids from the medium;

(c) optionally removing pigments and caffeine;

(d) extracting the resulting aqueous phase from (c) with an organic solvent and retaining the organic phase;

(e) optionally adding an aqueous medium to the organic phase and evaporating the organic phase, leaving an aqueous solution;

(f) removing the solvent from the thus obtained solution to obtain a dried product;

(g) dissolving the dried product in an organic solvent;

(h) eluting the mixture in a Sephadex column with an organic solvent as the eluting solvent;

(i) measuring the absorbence of successive fractions of the eluate at 280 nm ($E_{280}$);

(j) retaining one or more fractions that show a peak in $E_{280}$.

Further, the invention provides a process for obtaining an extract of tea having, in combination with a β-lactam antibiotic, a synergistic effect against MRSA, which process comprises:

(i) extracting tea into an aqueous medium;

(ii) optionally removing pigments and caffeine;

(iii) optionally further purifying the resulting aqueous medium (iv) fractionating the thus obtained product; and (v) retaining one or more fractions having the desired synergistic effect.

Yet further, the invention provides a tea extract obtainable by:

(a) extracting tea into an aqueous medium;

(b) removing solids from the medium;

(c) optionally removing pigments and caffeine;

(d) extracting the resulting aqueous phase from (c) with an organic solvent and retaining the organic phase;

(e) optionally adding an aqueous medium to the organic phase; and evaporating the organic phase, leaving an aqueous solution;

(f) removing the solvent from the thus obtained solution to obtain a dried product;

(g) dissolving the dried product in a further organic solvent;

(h) eluting the mixture in a Sephadex column using an organic solvent as the eluting solvent;

and retaining the fraction that, in combination with a β-lactam antibiotic, has the greatest synergistic activity against MRSA.

The invention also provides a method of treating patients infected with MRSA by administering, either simultaneously, separately or sequentially, to the patient an effective amount of an extract of tea or active fraction thereof with a β-lactam antibiotic.

The invention also provides the use of a β-lactam antibiotic and an extract of tea in the manufacture of a medicament for the treatment of MRSA infections in mammals including man.

The extract of tea or active fraction thereof and the β-lactam antibiotic may be packaged in a kit, optionally together with instructions for their administration. Such a kit forms a further aspect of the invention.

The combination of an extract of tea or active fraction thereof can also be packaged and used to treat other methicillin resistant bacterial infections mediated by PBP2'.

Suitable (β-lactam antibiotics which can be used include both penicillin-type and cephalosporin-type antibiotics. For example, suitable antibiotics include benzylpenicillin, ampicillin, methicillin, cloxacillin, flucloxacillin, cephalothin, cefamandole, cefazolin, cefuroxime, cefotaxime, and ceftriaxone. Preferred antibiotics include methicillin, flucloxacillin and cefazolin. Optionally, more than one antibiotic can be used in a combined preparation with an extract of tea.

In the present invention, the term "extract of tea" refers to the aqueous extract obtainable by mixing processed dried tea (such as black, green or oolong tea) with hot, preferably boiling water. The mixing is performed for a period of time sufficient to dissolve the water soluble components. With water or any other suitable aqueous buffer mixing at 90°–100° C. for from 1 to 10 minutes will be sufficient. The extract may be further processed to remove undissolved solids or to concentrate the aqueous extract. The aqueous extract may itself be processed and fractionated further. The aqueous fraction which contains polyphenols has been found to retain the synergistic activity of the complete aqueous fraction. This is not to say that the active principle(s) is/are polyphenol(s). Indeed, certain polyphenols that have been analysed do not retain all three activities of the tea extract. Rather, it establishes that the active principle(s) may be purified by purification of the polyphenol fraction of the extract, for example in accordance with the method of Robertson and Bendall (Phytochemistry(1983) 22;883–887).

Any suitable method may be used for purification of active fractions but, in general, tea is extracted into an aqueous medium, preferably water, more preferably boiling water and concentrated, for example in a rotary evaporator. Typically, this extract is filtered, centrifuged or otherwise treated to remove solids. Optionally, pigments and caffeine may be removed, preferably by extracting into a solvent such as chloroform. In this case, the organic layer containing the pigment and caffeine is discarded. The remaining aqueous phase may then be extracted into a further organic solvent, preferably ethyl acetate. This extraction may be repeated several times. The ethylacetate phase or phases thus obtained may then be concentrated, preferably in vacuo. Optionally, an aqueous medium, preferably an equal volume of water, may be added, and the remaining organic solvent evaporated, leaving an aqueous solution. The solvent is removed from the thus obtained solution, for example by freeze-drying in the case of an aqueous solution, and the solid is re-suspended in a further solvent. This solution is then loaded onto a separation column suited for use with organic solvents. Sephadex columns are preferred, with Sephadex™ LH-20 being particularly preferred. Elution of the mixture through the column generates a number of fractions. These can be analysed in any appropriate way in order to determine their biological properties (activities I, II and III), preferably by measuring the absorbence of successive fractions of the eluate at 280 nm. Typically, fractions having high activity are retained. The preferred fractions described below show peaks in $E_{280}$, though fractions that do not have a high $E_{280}$ but nonetheless have one or more of the three activities may also be retained.

In a preferred embodiment, the tea is extracted with boiling water, concentrated in a rotary evaporator and extracted with chloroform. The organic layer is discarded and the aqueous phase extracted eight times with ethyl acetate. The organic phases are combined, concentrated to 30 ml in vacuo, added to an equal volume of water and the remaining ethylacetate evaporated. The aqueous solution is freeze-dried, re-suspended in methanol, added to an equal volume of chloroform:petrol (1:1) and loaded onto a separation column, for example Sephadex™ LH-20 which has been equilibrated with chloroform: methanol: petrol (1:2:1). Fractions can be collected and freeze dried. The ethyl acetate fraction contains about 16% of the total dry weight of the aqueous extract. This fraction retained the synergistic activity.

An active fraction of tea extract is a fraction which substantially retains the synergistic activity of the entire extract may also be used in the present invention. The fractions may be produced by any other methods available in the art including that of Robertson and Bendall described above. Some preferred fractions are those described as Peaks # C, E, F, G, and Ha-Hc described in Example 6. Fractions F and G, especially G, are particularly preferred. Fractions can be tested to see if they retain synergistic activity by the methods described in Example 1 below.

The polyphenol compounds include catechins of the formula (I)

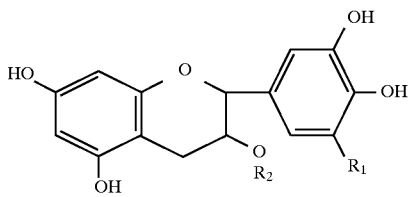

in which $R_1$ is a hydrogen atom or a hydroxy group and $R_2$ is a hydrogen atom or a 3,4,5-trihydroxy benzoyl group.

Particular examples of the tea catechin compounds represented by the general formula (I) include: (−)epicatechin, which is a compound of the formula (I) with $R_1$=H and $R_2$=H; (−)epigallocatechin, which is a compound of the formula (I) with $R_1$=OH and $R_2$=H; (−)epicatechin gallate, which is a compound of the formula (−) with $R_1$=H and $R_2$=3,4,5-trihydroxy benzoyl; and (−)epigallocatechin gallate, which is a compound of the formula (I) with $R_1$=OH and $R_2$=3,4,5-trihydroxy benzoyl group. Other polyphenols include gallic acid, theogallin, flavanols, such as quercetin, kaempferol, myricetin, and their glycosides; and depsides such as chlorogenic acid and p-coumarylquinic acid Theaflavins, which exist in, for example, black tea include compounds of the general formula (II)

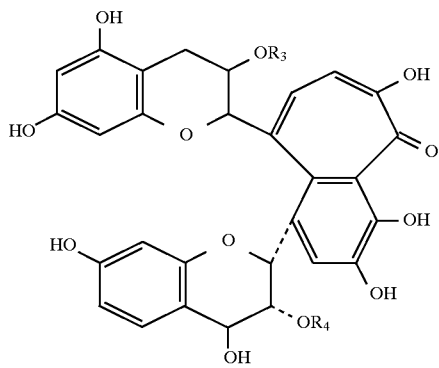

in which $R_3$ and $R_4$ are, independently from each other, hydrogen or 3,4,5-trihydroxy benzoyl. Particular examples of the theaflavin compounds include: free theaflavin, which is a compound of the formula (II) with $R_3$=H and $R_4$=H; theaflavin monogallate A, which is a compound of the formula (II) with $R_3$=3,4,5-trihydroxy benzoyl and $R_4$=H; theaflavin monogallate B, which is a compound of the formula (II) with $R_3$=H and $R_4$=3,4,5-trihydroxy benzoyl; and theaflavin digallate, which is a compound of the formula (II) with $R_3$=3,4,5-trihydroxy benzoyl and $R_4$=3,4,5-trihydroxy benzoyl group. Other compounds found in tea include thearubigins, theophylline, theobromine and caffeine, as well as possibly over 300 volatile flavour components at minor concentrations.

Some fractions of tea are commercially available. For example, Sunphenon™ from Taiyo Kagaka and Polyphenon 30, 100 and B from Mitsui Norin are commercially available preparations of catechins. Catechin is available from Sigma Chemical Company.

The combination of antibiotic and tea extract according to the invention may be administered to a patient infected with MRSA by any means conventional in the art. The route of administration will determine the amount of the antibiotic and tea extract to be administered. When the tea extract is to be used in an unfractionacted form, oral administration of the tea is excluded from the invention.

The antibiotic and the tea extract may be administered to mammals including humans by any route appropriate to the condition to be treated, suitable routes including oral, rectal, nasal, topical (including buccal and sublingual), vaginal and parenteral (including subcutaneous, intramuscular, intravenous, intradermal, intrathecal and epidural). It will be appreciated that the preferred route may vary with, for example, the condition of the recipient.

While it is possible for the compounds to be administered alone it is preferable to present them as pharmaceutical formulations. The formulations of the present invention comprise at least one active ingredient, as above defined, together with one or more acceptable carriers thereof and optionally other therapeutic ingredients. The carrier(s) must be "acceptable" in the sense of being compatible with the other ingredients of the formulation and not deleterious to the recipients thereof.

The formulations include those suitable the routes of administration described above. The formulations may conveniently be presented in unit dosage form and may be prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

For infections of the eye or other external tissues, e.g., mouth and skin, the formulations are preferably applied as a topical ointment or cream containing the active ingredient.

Formulations suitable for topical administration to the eye also include eye drops wherein the active ingredient is dissolved or suspended in a suitable carrier, especially an aqueous solvent for the active ingredient.

Formulations suitable for topical administration in the mouth include lozenges comprising the active ingredient in a flavoured base.

Formulations for rectal administration may be presented as a suppository with a suitable base.

Formulations suitable for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as for example a nasal spray or as nasal drops, include aqueous or oily solutions of the active ingredient.

Formulations suitable for vaginal administration may be presented as pessaries, tampons, creams, gels, pastes, foams or spray formulations.

Formulations suitable for parenteral administration include aqueous and non-aqueous sterile injection solutions. Injection solutions and suspensions may be prepared extemporaneously from sterile powders, granules and tablets of the kind previously described.

The above formulations may contain the antibiotic and tea extract of fraction thereof together or the two components may be prepared separately in different formulations. For example, it may be convenient to administer the tea extract topically, e.g. to an infected wound but to administer the antibiotic orally or by injection. The two components may be administered together in a single formulation or together in different formulations at the same time. Alternatively, the two ingredients may be administered sequentially within a period of time shorter enough to allow the synergistic effect to occur. Preferably, the sequential use of the two ingredients will require administration of both components within one hour of each other, preferably within five or ten minutes.

The amount of antibiotic to be administered will depend in part on the route of administration and the condition of the patient to be treated. Generally, antibiotic administered orally or by injection will be at a dose of from 10 to 200 mg/kg body weight per day, preferably 50 to 100 mg/kg per day. The amount will depend upon the condition of the patient and the potency of the particular antibiotic used. In compositions for topical administration the antibiotic will generally be present at a concentration of 0.1 to 5% w/w, preferably 0.5 to 3% w/w. In general, the amount of antibiotic present in a formulation for administration to a patient will be such that the dose of antibiotic administered is similar to that required to inhibit the growth or kill strains of S. aureus which do not have the MRSA phenotype and below the dose required to inhibit the growth of or kill MRSA.

The amount of tea extract to be administered will depend upon the concentration of the extract and the type of tea. Suitable types of tea include Japanese (Sencha) tea which is a green leaf tea as well as black tea.

In the experiments described below a 2% extract (2 g of tea in 100 ml water) of crushed leaf tea made in boiling water was used as a source of extract and dilutions of this were capable of enhancing the activity of methicillin. The weights and concentrations of extract given below all refer back to the weight of leaf tea dissolved in the aqueous extract, unless otherwise specified. A $\frac{1}{200}$ dilution of the 2% extract was found to be effective in enhancing the activity of methicillin. Thus, direct application of tea extract to provide topical concentrations of at least 10–100 $\mu$g/ml, e.g. 20–50 $\mu$g/ml at the desired site of action are effective in enhancing the activity of β-lactam antibiotics in treating MRSA. Since tea is generally regarded as non-toxic at the concentrations at which it is made or drunk (about 3 mg/ml) it is possible to use much higher concentrations than 100 $\mu$g/ml of tea. For example concentrations of up to 1 mg/ml, for example 10 mg/ml, 100 mg/ml or 1 g/ml. Where a specific fraction of tea is to be used, the amount of the fraction will be in proportion to its concentration in the extract of whole tea. For example, about one third of the extract is polyphenols. When the fraction which includes the polyphenols is used the concentrations mentioned above may be reduced by one-third. Concentrations of the tea extract of fractions thereof for injectable or oral compositions will be designed to deliver similar amounts of tea to the site where its action is required. Suitable daily doses of whole extract will be in the region of from about 10 to about 1000 mg/kg body weight, e.g. about 50 to 100 mg/kg body weight.

Both the antibiotic and tea may be administered in unit dosage form and the suitable daily doses may be presented as a single dose or in divided doses, for example 2, 3 or 4 sub-doses administered at appropriate intervals throughout the day.

The following Examples illustrate the invention and demonstrate the three components of the activity of extracts of tea against MRSA. They show that an extract of tea is effective in rendering MRSA sensitive to concentrations of methicillin between 8 and 128 times less than usually required to inhibit the growth of MRSA. The effect is a specific synergistic effect with tea. Tea exerts its synergistic effect even at concentrations where it has no direct antibacterial effect. This is demonstrated by the fact that no synergy is found when tea is used with methicillin on methicillin sensitive S. aureus (MSSA). Control experiments using a second antibiotic, vancomycin, in place of tea show no synergistic effect whatever.

EXAMPLE 1

Materials 20 strains of MRSA (isolated in Australia, Brazil, Chile, Denmark and Germany) that are highly resistant to methicillin (i.e. at least 128 $\mu$g/ml is required to inhibit them) were tested.

A 2% extract of crushed leaf Japanese "Sencha" tea was made in boiling water, and filtered through a Millipore filter. This extract contains about 14.7 mg/ml of tea.

Sodium methicillin (SmithKline Beecham) and vancomycin hydrochloride (Lilly Industries) were Laboratory Reference preparation.

IsoSensitest agar (Unipath CM 471) was supplemented with 20 g NaCl/L.

Methods

Strains were grown overnight at 37° C. in IsoSensitest™ broth (ISB, Unipath CM 473), and 1 $\mu$l amounts (c. $10^6$ colony forming units (cfu) were inoculated on to six series of plates of IsoSensitest™ agar containing doubling dilutions of methicillin (1024- 1 $\mu$g/ml) alone and in the presence of tea extract in various sub-inhibitory concentrations, viz final dilutions of $\frac{1}{40}$, $\frac{1}{70}$, $\frac{1}{100}$, $\frac{1}{200}$ and $\frac{1}{300}$.

A similar experiment was done using methicillin diluted in a series of sub-inhibitory concentrations of vancomycin, namely 0.5, 0.28, 0.2, 0.1 and 0.07 $\mu$g/l.

Plates were incubated at 30° for 48 h. The minimum inhibitory concentration (MIC) of antibiotic was calculated for each sample, as a measure of activity II.

Results

Tea extract at $\frac{1}{300}$ had no effect on methicillin MICs. However, the higher concentrations all markedly reduced the MIC of methicillin for all the strains, by between 8 and 3 dilution steps (i.e. from 128- to 8 fold). The majority of strains became sensitive to 2, 4 or 8 $\mu$g/ml methicillin in the presence of the extracts; in the absence of the extract, MICs were usually 512 $\mu$g/ml.

Results were summarized in Table 1. There was no reduction in methicillin MIC in the presence of vancomycin.

Comparative Example 1

The antimicrobial spectrum of tea extracts (Activity I) was determined by a well diffusion method. Plates of IsoSensitest agar (Oxoid) were spread with cultures diluted so that the final inoculum was c. $10^5$ cfu/plate. 6 mm wells were cut from the agar and filled with 100 $\mu$l of extracts of tea obtained in accordance with Example 1. Zones of inhibition were measured after overnight incubation.

The titre of extracts (i.e. the dilution that just failed to produce a zone of inhibition) was determined by assaying serial dilutions of extracts, as above, and calculating the intercept giving zero zone size of the regression line. This figure (a dilution factor) was converted into a Maximal Non-Inhibitory Concentration (MNIC, Cooper 1963 in Analytical Microbiology (Ed Kavanagh) London, Academic Press) by reference to the known concentration of solids in the original extract.

MICs were determined by the tube dilution method in 1 ml volumes of IsoSensistest broth (Oxoid), with an inoculum of $10^5$ cfu/tube. Tubes were read for growth after overnight incubation, and then MBC (at least 99.9% kill) was determined by subculture of 0.2 ml from each tube (endpoint: growth of <20 colonies). Fifteen strains of MRSA were tested. The MNIC was found to be 190±50 µg/ml. The MIC was 280 µg/ml and the minimum bactericidal concentration (MBC) was 410 µg/ml. This is in contrast to Examples 1 above and 2 below where concentrations of as little of 50 µg/ml of extract are sufficient to render some MRSA sensitive to methicillin.

EXAMPLE 2

A further 20 strains of low level MRSA were tested for activity II according to the procedures described in Example 1. The results are shown in Table 2. The table shows that even the presence of a 1/300 of tea dilution had an effect on the ability of methicillin to inhibit the growth of MRSA.

EXAMPLE 3

Two strains of MRSA, one of which, 13136p$^-$M$^+$, (A) is constitutive, the other, (B) inducible, for its production of PBP2' were studied, with a view to measuring activity II.

Strains were grown in broth (A) alone or +25 µg/ml tea extract; (B)+methicillin 100 µg/ml [as inducer]±tea extract 25 µg/ml. Strains were harvested, and PBPs extracted and analyzed (by gel electrophoresis, following labelling with $^{14}$C-benzylpenicillin), as previously described (Brown DFJ & Reynolds PE 1980: Intrinsic resistance to β-lactam antibiotics in Staphylococcus aureus. (FEBS Letters 122;275–278)).

The results showed that production of PBP2' was completely prevented in B and was inhibited by >90% in A.

EXAMPLE 4

A Staph. aureus strain was grown in broth+1 µg/ml methicillin [inducing agent]. β-lactamase activity was measured, using nitrocefin, in the presence and absence of tea (Gaisford W. C. & Reynolds P. E., 1989. Methicillin resistance in Staphylococcus epidermidis. Relationship between the additional penicillin-binding protein and an attachment transpeptidase. European J. Biochem. 185;211–218.) Little or no effect was found on the activity of the preformed enzyme. The strain was grown in the presence of inducing agent and of tea extract (25 µg/ml), the culture separated by centrifugation into cells and supernate, and the fractions assayed for β-lactamase activity as above. Tea prevented the induction of enzyme by about 60% and what was induced remained cell-bound as opposed to being excreted into the supernate. There was an 80–90% inhibition of the enzyme secretion into the supernatant fraction over 4 generations.

This finding demonstrates activity III and indicates that the combination of tea and benzylpenicillin may be synergistic; the reduced amount of β-lactamase present in cultures grown in tea is less able to protect the bacteria from the lethal action of benzylpenicillin.

EXAMPLE 5

The 40 strains tested in Examples 1 and 2 above, together with 9 strains of methicillin-sensitive Staph. aureus (MSSA) were tested for their resistance to benzylpenicillin in the presence or absence of tea extract, with a view to measuring activity III. The procedures used were those described in Example 1, except that benzylpenicillin replaced methicillin. Both MSSA and MRSA have natural resistance to benzylpenicillin through the production of β-lactamase.

The results are shown in Table 3. It can be seen that dilutions from T/300 to T/40 (approximately from 50 to 370 µg/ml extract) of tea were sufficient to synergise the activity of benzylpenicillin.

EXAMPLE 6

Determination of three different biological activities in tea extracts and in pure compounds known to be tea components
Method Chemicals. Epigallocatechin (EGC) and epigallocatechin gallate (EGCG) were bought from Funakoshi Ltd. Tokyo; epicatechin, chlorogenic acid, gallic acid, theobromine, theophylline, quercitin, and kaempferol were bought from Sigma. In this Example and generally, the term "petrol" refers to petroleum ether. The specific petroleum ether used in the method described below was "BDH Petroleum Spirit Technical", having a boiling range of 54° C. to 93° C.
Fractionation of tea extracts 30 g of Sencha (Japanese green tea, from "Wittards of Chelsea") was crushed in a mortar and extracted with 500 ml boiling water for 10 min; the mixture was filtered and the residue extracted again as before. The liquid phases were combined and evaporated under vacuum to a volume of approximately 100 ml. Pigments and caffeine were removed by 5 consecutive partitions into $CHCl_3$. The aqueous phase was centrifuged and the supernatant extracted 8 times with 200 ml ethyl acetate. The organic phases were combined and concentrated to a volume of around 30 ml under vacuum; an equal volume of water was added and the remainder of the ethyl acetate evaporated. The resulting aqueous phase was freeze-dried.

1 g of the thus obtained solid was dissolved in 1.5 ml methanol, and an equal volume of petrol/$CHCl_3$ (1:1) added creating a 2:1:1 solution of methanol/petrol/$CHCl_3$. This was loaded onto a column (2.5×47 cm) of Sephadex LE-20 (Registered trademark) equilibrated with methanol/petrol/$CHCl_3$ (2:1:1), and eluted under gravity using the same solvent. The flow rate was adjusted to 1 ml/min using a constant head device. Fractions of 10 ml were collected, and E280 nm of each measured.

After 194 fractions had been collected, the running phase was changed to methanol alone; this washed out material still left on the column, giving peak #H.

The elution profile is shown as FIG. 1. The fractions making up each of the numbered peaks (#A–Hc) were pooled separately and freeze-dried. They were stored at 4° C. in tightly stoppered jars wrapped in foil.

The fractions were assayed for activities I, II and III, as described below.
Determination of biological activities Activities I (inhibitory/killing actions against bacteria), II (anti-PBP2' action) and III (action against β-lactamase) were quantitated by bioassay, using large plates (14 cm diameter circular, or 25×25 cm square) containing IsoSensitest agar (Unipath CM 471) to a depth of about 4 mm. surface-seeded with S. aureus. Assay strains and additions to agar varied according to the activity being assayed (Table 4).

6 mm wells were cut into the agar and filled with appropriate dilutions (in duplicate) of solutions of the material to be assayed. Following overnight incubation, diameters of inhibition zones were measured, and plots made of (log concentration) vs zone diameter. MNIC was calculated by extrapolating the regression line to zone diameter=6 mm; it was expressed ether as a concentration (µg/ml) or an activity (reciprocal of concentration in mg/ml).
Results Biological activities of pure compounds. Epicatechin, chlorogenic acid, gallic acid, theobromine and theophylline showed no evidence of activity I or II when tested at 1 mg/ml.

Quercitin (MNIC=175 pg/ml; activity=5.7), kaempferol (>200; <5). EGC (50; 20) and EGCG (84; 12) showed a moderate amount of activity I, but no activity II.

Fractionation of tea extracts. The elution profile from the column is shown as FIG. 1, and the distribution of activities I, II and III between the various peaks is given in Table 5.

Activity I It is clear that activity I is spread widely across the fractions; most is in peak #E which, corresponds to EGC+EGCG. However, it should be noted that Quantitatively, #E shows greater activity I than if it were pure EGC (see above). Thus, activity I found here in tea extract is due not only to EGC and EGCG, but also to other compounds.

This conclusion is supported by another experiment. 17 different types and brands of tea leaf were extracted as a nominal 2%. E 272 nm, the absorption maximum for EGC and EGCG, was measured for each extract, as was dry weight (after freeze-drying), and biological activity (activity I) vs *Staph. aureus* Oxford. Correlation between these three parameters was then investigated by regression analysis. There was statistically significant correlation only between E272 and dry weight. This shows that (i) most of the dry weight was due to ECG+EGCG; (ii) activity I was not correlated with content of EGC+ECGC.

Activity II Activity II is at a maximum in peak # G, and is clearly separated from activity I. The principle(s) responsible for activity II must have great intrinsic activity, because as little as 2 $\mu$g/ml of crude peak # G still showed the effect.

Activity III Activity III seems to run parallel with activity II, both qualitatively and quantitatively.

Comparative Example 2

Experiments with "anti PBP2' principle" of Tajima et al

Background Tajima et al (Microbiol. Immunol. 37: 695–703, 1993; ibid 38: 639–648, 1994) reported that a compound derived from a mixture of tungstate and phosphate inhibited the formation of PBP2' by MRSA, thus sensitizing them to methicillin. For comparison purposes, some "Factor T" was made and compared with tea extracts.

Methods

Chemicals were bought from Sigma, and the method for making "Factor T" described by Tajima et al (1994) was followed closely. The factor T produced was assayed for activities I, II and III as described above.

Results

MNIC for activity I of "Fraction T" was found to be 60 pg/ml (i.e. it has about 50% the activity in this respect of peak E of our tea extract). However, at this concentration it showed no activity II and III, and is thus at least 30 times less active in this respect than our tea extract.

Conclusions

"Factor T" differs quantitatively and qualitatively from the tea extracts described herein. Any resemblance between the two is purely coincidental.

EXAMPLE 8

Mathematical analysis of data in Tables 1–3

The amount of synergy occurring between various concentrations of tea extract and methicillin vs MRSA (20 high level and 20 low level)—activity II—and between the same concentrations and benzylpenicillin vs 49 strains of bla+ *S. aureus*—activity III—has now been quantified in numerical terms.

This was done by calculating $\Sigma$FIC for each endpoint shown in these Tables. "Synergy" was defined as a value of $\Sigma$FIC<0.7 (i.e. at least a three-fold reduction in the MIC for both individual antibacterial agent). Details of this procedure can be found in Kerry et al (1975; J. Antimicrob. Chemother. 1: 417–427).

Activity II For all the 20 high level MRSA, tea extract at concentrations T/70, T/100 and T/200 caused synergy with methicillin. Maximum synergy was found for 15 strains with T/200 ($\Sigma$FIC=0.22–0.29), and for 5 with T/100 ($\Sigma$FIC= 0.38–0.45). The greatest degree of synergy observed was $\Sigma$FIC=0.22 (i.e. 10-fold reduction in MIC of each partner).

For all 20 low level strains tested, tea extract at concentrations T/70–T/300 showed synergy with methicillin. Maximum synergy ($\Sigma$FIC 0.17–0.36) was found for 6 strains with T/300, and for 14 with T/200 ($\Sigma$FIC 0.18–0.29). The greatest degree of synergy was $\Sigma$FIC=0.17.

Activity III 49 strains were tested here—a mixture of MRSA and MSSA. Synergy was observed between at least one concentration of tea extract and benzylpenicillin for 43 of the strains (88%). Maximum synergy ($\Sigma$FIC=0.14–0.36) was found with T/300 for 10 strains, with T1200 for 14 ($\Sigma$FIC=0.38–0.61), and with T/70 for 9 strains ($\Sigma$FIC= 0.52–0.59). The greatest degree of synergy seen was $\Sigma$FIC= 0.14.

TABLE 1

Effect of tea on activity of methicillin against high level MRSA

| Strain no. | MIC of methicillin ($\mu$g/ml) | | | | | |
|---|---|---|---|---|---|---|
| | alone | +T/40 | +T/70 | +T/100 | +T/200 | +T/300 |
| 1 | 512 | 8 | 16 | 16 | 64 | 512 |
| 2 | 256 | 4 | 8 | 8 | 32 | 128 |
| 3 | 512 | 4 | 4 | 4 | 32 | 512 |
| 4 | 512 | 8 | 16 | 16 | 64 | 256 |
| 5 | 512 | 2 | 4 | 8 | 64 | 512 |
| 6 | 512 | 4 | 16 | 16 | 64 | 512 |
| 7 | 512 | 4 | 8 | 16 | 32 | 512 |
| 8 | 512 | 4 | 8 | 16 | 32 | 512 |
| 9 | 512 | 2 | 8 | 16 | 32 | 128 |
| 10 | 256 | 2 | 8 | 8 | 32 | 256 |
| 11 | 512 | 2 | 8 | 16 | 64 | 512 |
| 12 | 512 | 4 | 8 | 8 | 32 | 512 |
| 13 | 128 | 4 | 4 | 8 | 16 | 128 |
| 14 | 512 | 8 | 16 | 32 | 128 | 512 |
| 15 | 256 | 4 | 8 | 16 | 128 | 512 |
| 16 | 256 | 2 | 2 | 4 | 32 | 256 |
| 17 | 1024 | 8 | 8 | 16 | 128 | 1024 |
| 18 | 256 | 16 | 16 | 16 | 64 | 256 |
| 19 | 128 | 16 | 16 | 16 | 64 | 256 |
| 20 | 1024 | 16 | 32 | 64 | 256 | 512 |
| % strains converted to "sensitive"* | | 85% | 65% | 35% | 0 | 0 |

*by US definition, ie MIC $\leq$ 8 $\mu$g/ml

TABLE 2

Effect of tea on activity of methicillin against low level MRSA.

| Strain no. | MIC of methicillin ($\mu$g/ml) | | | | | |
|---|---|---|---|---|---|---|
| | alone | +T/40 | +T/70 | +T/100 | +T/200 | +T/300 |
| 1 | 32 | 1 | 2 | 4 | 4 | 8 |
| 2 | 128 | 2 | 8 | 8 | 16 | 32 |
| 3 | 128 | 4 | 4 | 8 | 16 | 16 |
| 4 | 32 | 1 | 4 | 4 | 8 | 16 |
| 5 | 256 | 1 | 16 | 32 | 32 | 64 |
| 6 | 256 | 2 | 8 | 32 | 16 | 64 |
| 7 | 256 | 1 | 4 | 8 | 16 | 16 |
| 8 | 256 | 4 | 8 | 8 | 16 | 32 |
| 9 | 128 | 4 | 8 | 8 | 16 | 32 |
| 10 | 128 | 1 | 4 | 8 | 16 | 32 |

TABLE 2-continued

Effect of tea on activity of methicillin against low level MRSA.

| | MIC of methicillin (μg/ml) | | | | |
|---|---|---|---|---|---|
| Strain no. | alone | +T/40 | +T/70 | +T/100 | +T/200 | +T/300 |
| 11 | 128 | 1 | 4 | 8 | 8 | 32 |
| 12 | 128 | 1 | 2 | 2 | 2 | 8 |
| 13 | 128 | 1 | 8 | 8 | 16 | 32 |
| 14 | 128 | 1 | 4 | 4 | 4 | 8 |
| 15 | 128 | 8 | 16 | 32 | 32 | 32 |
| 16 | 128 | 2 | 8 | 8 | 16 | 32 |
| 17 | 64 | 2 | 4 | 4 | 8 | 16 |
| 18 | 32 | 1 | 2 | 4 | 4 | 8 |
| 19 | 128 | 1 | 8 | 8 | 16 | 16 |
| 20 | 128 | 4 | 8 | 8 | 16 | 32 |
| % strains converted to "sensitive" | 100% | 90% | 85% | 35% | 20% | |

TABLE 3

Resistance of various strains of S. aureus to benzylpenicillin in the presence and absence of tea extract.

| | MIC of benzylpenicillin (μg/ml) | | | | | |
|---|---|---|---|---|---|---|
| Strain no. | alone | +T/40 | +T/70 | +T/100 | +T/200 | +T/300 |
| MRSA | | | | | | |
| 1 | 32 | 2 | 4 | 4 | 16 | 32 |
| 2 | >512 | 32 | 64 | 256 | 256 | 128 |
| 3 | >512 | 256 | 256 | 512 | >512 | >512 |
| 4 | >512 | 256 | 256 | 256 | 256 | 512 |
| 5 | >512 | 32 | 64 | 128 | 256 | >512 |
| 6 | >512 | 128 | 128 | 256 | 512 | 512 |
| 7 | >512 | 32 | 256 | 512 | 512 | >512 |
| 8 | >512 | 128 | 256 | 512 | 512 | >512 |
| 9 | 64 | 0.06 | 2 | 4 | 16 | 64 |
| 10 | >512 | 32 | 128 | 256 | 512 | >512 |
| 11 | >512 | 128 | 256 | 512 | >512 | 512 |
| 12 | >512 | 128 | 128 | 256 | >512 | >512 |
| 13 | >512 | 16 | 64 | 64 | 256 | 256 |
| 14 | >512 | 256 | 256 | 512 | >512 | 512 |
| 15 | 512 | 32 | 64 | 128 | 256 | 256 |
| 16 | 64 | 0.06 | 0.25 | 1 | 16 | 32 |
| 17 | >512 | 64 | 128 | 256 | 512 | >512 |
| 18 | >512 | 64 | 128 | 128 | 512 | 512 |
| 19 | 16 | 0.03 | 1 | 1 | 4 | 16 |
| 20 | >512 | 256 | 512 | 512 | >512 | 256 |
| MRSA LL | | | | | | |
| 1 | 128 | 2 | 16 | 64 | 64 | 32 |
| 2 | >512 | 16 | 64 | 128 | 128 | 512 |
| 3 | 512 | 64 | 64 | 128 | 256 | 512 |
| 4 | 512 | 32 | 64 | 128 | 256 | 128 |
| 5 | >512 | 8 | 64 | 128 | 512 | 512 |
| 6 | >512 | 8 | 64 | 128 | 512 | 512 |
| 7 | >512 | 8 | 64 | 128 | 256 | 512 |
| 8 | >512 | 128 | 128 | 256 | 512 | 512 |
| 9 | >512 | 256 | 128 | 256 | 512 | 512 |
| 10 | 512 | 0.06 | 0.25 | 1 | 4 | 8 |
| 11 | >512 | 16 | 64 | 256 | 256 | 256 |
| 12 | >512 | 2 | 4 | 32 | 128 | 128 |
| 13 | 512 | 4 | 32 | 32 | 128 | 64 |
| 14 | 8 | 0.03 | 0.25 | 0.25 | 0.5 | 1 |
| 15 | 16 | 1 | 1 | 2 | 4 | 4 |
| 16 | >512 | 64 | 256 | 256 | 512 | 256 |
| 17 | 512 | 32 | 16 | 64 | 256 | 256 |
| 18 | 8 | 0.03 | 0.13 | 0.25 | 0.5 | 0.5 |
| 19 | 256 | 16 | 64 | 64 | 128 | 128 |
| 20 | >512 | 64 | 64 | 64 | 256 | 256 |
| MSSA | | | | | | |
| 1 | >512 | 8 | 64 | 128 | 128 | 256 |
| 2 | 512 | 4 | 16 | 32 | 64 | 128 |
| 7 | 512 | 0.5 | 2 | 8 | 8 | 16 |
| 8 | 512 | 0.5 | 4 | 8 | 16 | 32 |
| 9 | 32 | 0.13 | 2 | 4 | 8 | 16 |
| 11 | 256 | 2 | 4 | 8 | 16 | 16 |
| 17 | 32 | 0.25 | 0.25 | 0.5 | 1 | 2 |
| 18 | 16 | 1 | 2 | 4 | 8 | 8 |
| 20 | 4 | 0.03 | 0.06 | 0.13 | Contam | Contam |

TABLE 4

Methods used for measurement of biological activities of tea fractions and pure compounds.

| Activity | Indicator strain | Inoculum* | Additions to agar | Incubation temperature |
|---|---|---|---|---|
| I | S. aureus Oxford (bla⁻methi-S) | 1/100 | nil | 37° C. |
| II | S. aureus USA#18 | 1/50 | methicillin 10 μg/ml | 30° C. |
| III | S. aureus 16084 (bla⁺methi-S) | 1/80 | benzylpenicillin 1 μg/ml | 37° C. |

*agar surface was flooded with indicated dilution of overnight broth culture, which was sucked off immediately, and plates dried for 20 min
Note 1
bla⁻ = does not produce β-lactamase
bla⁺ = produce β-lactamase
Note 2
Activity II is determined with 30° C. incubation temperature as PBP2' is expressed well under such conditions.

TABLE 5

Activities I, II and III in various chromatographic fractions

| | | Chromatographic pool | | | | | | | | |
|---|---|---|---|---|---|---|---|---|---|---|
| | | A | B | C | D | E | F | G | Ha | Hb | Hc |
| Mass | (mg) | 1.5 | 19.6 | 95.1 | 58.8 | 254.5 | 15.1 | 24.1 | 61.1 | 134.5 | 10.6 |
| Activity I | (1/"critical concn" | — | — | 10 | — | 38.5 | 7.1 | 20 | 30 | 24 | 19.3 |

TABLE 5-continued

Activities I, II and III in various chromatographic fractions

| | | Chromatographic pool | | | | | | | | | |
|---|---|---|---|---|---|---|---|---|---|---|---|
| | | A | B | C | D | E | F | G | Ha | Hb | Hc |
| Activity II | in mg/ml) (1/"critical concn" in mg/ml) | | | — | — | — | 98 | 571 | c 33 (sum of Ha, Hb and Hc) | | |
| Activity III | (1/"critical concn" in mg/ml) | | | — | — | — | 154 | 555 | c 33 (sum of Ha, Hb and Hc) | | |

— = negligible activity
blank = not done

I claim:

1. A method of treating a bacterial infection of a human or animal by inhibiting production of PBP2' by bacteria infecting the human or animal, said bacteria selected from
   bacteria which constitutively express PBP2' and
   bacteria which inducibly express PBP2' in the presence of a β-lactam antibiotic,
   said method comprising administering simultaneously, separately or sequentially a β-lactam antibiotic and an effective amount of an extract of tea to said human or animal, said extract of tea comprising at least one active principle of dried tea and being extractable from processed dried tea with hot water and said active principle being capable, on administration to MRSA, of restoring the activity against said methicillin-resistant *Staphylococcus aureus* (MRSA) of a β-lactam antibiotic.

2. A method according to claim 1 wherein said β-lactam antibiotic is selected from the group consisting of methicillin, cloxacillin, flucloxacillin, cephalothim, cefamandole, cefazolin, cefuroxime, cefotaxime and ceftriaxone.

3. A method according to claim 2 wherein said β-lactam antibiotic is methicillin.

4. A method according to claim 2 wherein said β-lactam antibiotic is flucloxacillin.

5. A method according to claim 2 wherein said β-lactam antibiotic is cefazolin.

6. A method according to claim 1 comprising administering an extract of tea and a β-lactam antibiotic simultaneously, for the treatment of methicillin-resistant *Staphylococcus aureus* (MRSA) infections in an animal, including man, in a quantity producing a synergistic antibacterial effect.

7. A method according to claim 6 comprising administering an extract of tea and a β-lactam antibiotic separately, for the treatment of methicillin-resistant *Staphylococcus aureus* (MRSA) infections in an animal, including man, in a quantity producing a synergistic antibacterial effect.

8. A method according to claim 1 comprising administering an extract of tea and a β-lactam antibiotic sequentially, for the treatment of methicillin-resistant *Staphylococcus aureus* (MRSA) infections in an animal, including man, in a quantity producing a synergistic antibacterial effect.

9. A method according to claim 2 wherein the tea extract is obtainable by
   (a) extracting tea into an aqueous medium;
   (b) removing solids from the medium;
   (c) removing pigments and caffeine;
   (d) extracting the resulting aqueous phase from (c) with an organic solvent and retaining the organic phase;
   (e) adding an aqueous medium to the organic phase and evaporating the organic phase, leaving an aqueous solution;
   (f) removing the solvent from the thus obtained solution to obtain a dried product;
   (g) dissolving the dried product in an organic solvent;
   (h) eluting the mixture in a Sephadex column equilibrated with an organic solvent as the eluting solvent;
   (i) measuring the absorbence of successive fractions of the eluate at 280 nm ($E_{280}$); and
   (j) retaining a fraction that shows a peak in $E_{280}$.

10. A method according to claim 9 wherein the tea extract is obtainable by
    (a) extracting tea into an aqueous medium;
    (b) removing solids from the medium;
    (c) removing pigments and caffeine;
    (d) extracting the resulting aqueous phase from (c) with an organic solvent and retaining the organic phase;
    (e) adding an aqueous medium to the organic phase and evaporating the organic phase, leaving an aqueous solution;
    (f) removing the solvent from the thus obtained solution to obtain a dried product;
    (g) dissolving the dried product in an organic solvent;
    (h) eluting the mixture in a Sephadex column equilibrated with an organic solvent as the eluting solvent;
    (i) measuring the absorbence of successive fractions of the eluate at 280 nm ($E_{280}$); and
    (j) retaining one or more fractions from the sixth peak in $E_{280}$.

11. A method of treating MRSA infections in a patient which comprises administering, simultaneously, separately or sequentially, to the patient a synergistic amount of an extract of tea or active fraction thereof and a β-lactam antibiotic.

12. A method of treating MRSA infections in a patient comprising administering simultaneously, separately or sequentially, to the patient a β-lactam antibiotic and an effective amount of an extract of tea comprising at least one active principle of dried tea and being extractable from processed dried tea with hot water, said active principle being capable, on administration to MRSA, of restoring the activity against methicillin-resistant *Staphylococcus aureus* (MRSA) of a β-lactam antibiotic.

* * * * *